United States Patent [19]

McCall

[11] 4,140,775
[45] Feb. 20, 1979

[54] PIPERAZINO METHYL PHENYL AMINOQUINOLINES

[75] Inventor: John M. McCall, Kalamazoo, Mich.

[73] Assignee: The Upjohn Company, Kalamazoo, Mich.

[21] Appl. No.: 903,199

[22] Filed: May 5, 1978

[51] Int. Cl.² ................... A61K 31/495; C07D 295/12
[52] U.S. Cl. ..................................... 424/250; 544/363
[58] Field of Search ......................... 544/363; 424/250

[56] References Cited

U.S. PATENT DOCUMENTS

| | | | |
|---|---|---|---|
| 2,474,820 | 7/1949 | Burckhalter et al. | 544/363 |
| 3,992,382 | 11/1976 | Coverdale et al. | 424/250 |
| 4,025,629 | 5/1977 | Coverdale | 544/363 |

Primary Examiner—Paul M. Coughlan, Jr.
Attorney, Agent, or Firm—Hans L. Berneis

[57] ABSTRACT

Antihypertensive compounds of the formula III

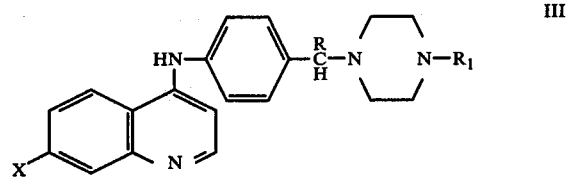

wherein X is chloro or trifluoromethyl; wherein R is hydrogen or alkyl of 1 to 3 carbon atoms, inclusive; wherein $R_1$ is phenyl or phenyl substituted with one or two alkyl, alkoxy, trifluoromethyl or halo substituents, in which alkyl and alkoxy are each of 1 to 3 carbon atoms, inclusive, and halo is fluoro, chloro or bromo, are prepared by reacting a 4-chloro-7-substituted quinoline of formula I with a compound of the formula II

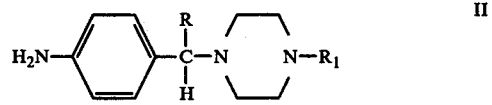

wherein R and $R_1$ are defined as above. The pharmacologically acceptable acid addition salts of compounds of formula III can also be used as antihypertensive agents.

22 Claims, No Drawings

PIPERAZINO METHYL PHENYL AMINOQUINOLINES

BRIEF SUMMARY OF THE INVENTION

FIELD OF THE INVENTION

This invention relates to new organic antihypertensive compounds and is particularly concerned with 4-substituted piperazinomethylphenylaminoquinolines III.

The new compounds and the processes of this invention can be illustratively represented by the following schemes:

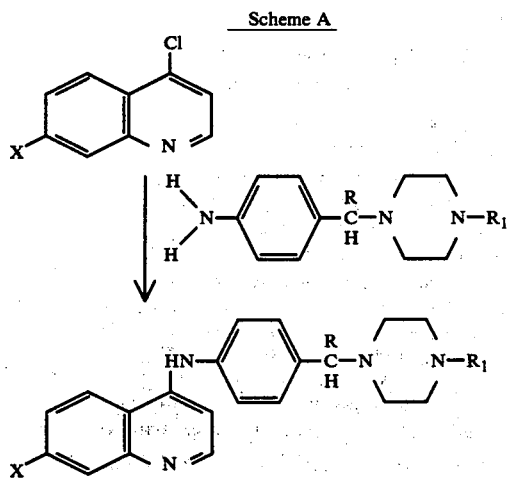

wherein X is chloro or trifluoromethyl; wherein R is hydrogen or alkyl of 1 to 3 carbon atoms, inclusive; wherein $R_1$ is phenyl or phenyl substituted with one or two alkyl, alkoxy, trifluoromethyl or halo substituents, in which alkyl and alkoxy are each of 1 to 3 carbon atoms, inclusive, and halo is fluoro, chloro or bromo.

The reagents II are either known in the art or can be produced by Scheme B:

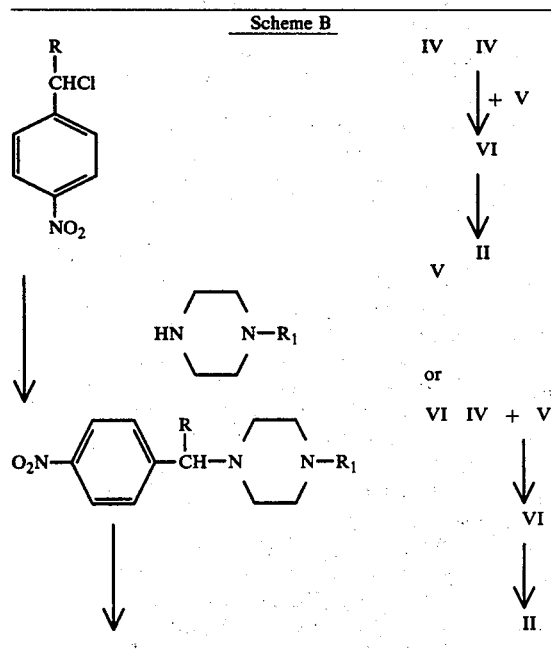

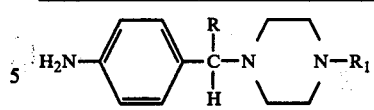

wherein R and $R_1$ have the significance of hereinabove.

The new compounds embraced by this invention are therefore of the formula III

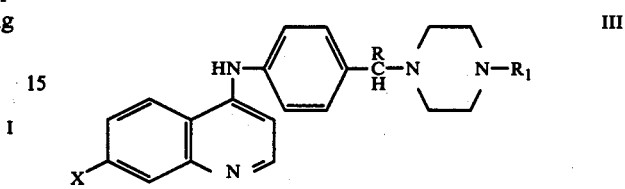

wherein X is chloro or trifluoromethyl; wherein R is hydrogen or alkyl of 1 to 3 carbon atoms, inclusive; wherein $R_1$ is phenyl or phenyl substituted with one or two alkyl, alkoxy, trifluoromethyl or halo substituents, in which alkyl and alkoxy are each of 1 to 3 carbon atoms, inclusive, and halo is fluoro, chloro or bromo, or the pharmacologically acceptable acid addition salts thereof.

The preferred compounds of this invention are those of the formula IIIA

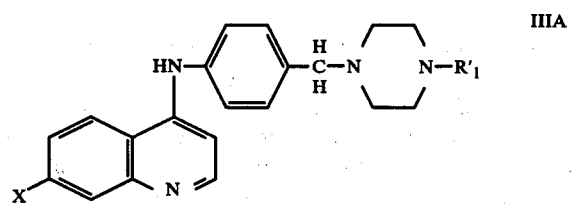

wherein X is chloro or trifluoromethyl; wherein $R'_1$ is phenyl or phenyl substituted with one or two alkyl, alkoxy, trifluoromethyl or halo substituents, in which alkyl and alkoxy are each of 1 to 3 carbon atoms, inclusive, and halo is fluoro, chloro or bromo, or the pharmacologically acceptable acid addition salts thereof.

The most preferred compounds of this invention are of the formula IIIB

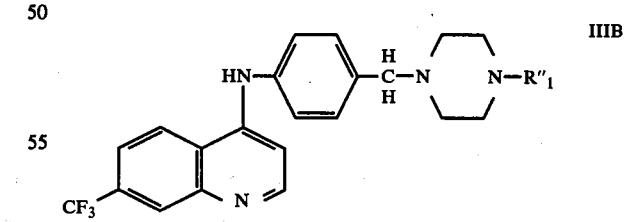

wherein $R''_1$ is phenyl substituted by one or two alkyl, alkoxy or halo, in which alkyl and alkoxy are each of 1 to 3 carbon atoms, inclusive, and halo is fluoro or chloro, or the pharmacologically acceptable acid addition salts thereof.

When R is alkyl of 1 to 3 carbon atoms, the methylene carbon in formula III possesses chirality; the scope of this invention is not intended to be limiting to a particular optically active isomer.

The compounds of formula III or their acid addition salts in their crystalline state can be isolated as solvates, i.e., with a discreet quantity of solvent, e.g., water, ethanol, and the like, associated physically, and thus removable without effective alteration of the chemical entity per se.

The following related patents were considered: U.S. Pat. No. 2,474,818 showing:

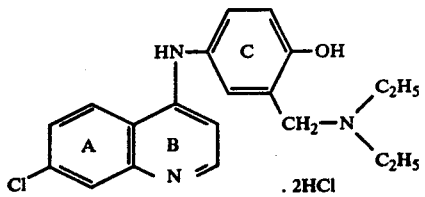

Amodiaquin (Camoquin) which is an antimalarial (also reported *J. Am. Chem. Soc.* 70, 1363, 1948); and

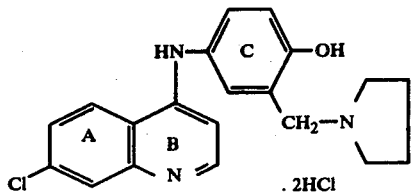

Amopyroquine, U.S. Pat. Nos. 2,474,820 and 2,474,821, which also is an antimalarial compound. The compounds disclosed in the above patents differ from the present ones by having an o- or p-hydroxy group on the phenyl ring "C" and the methylene-N-substituted group in the m-position of the phenyl ring "C". Further, in the generic disclosure of U.S. Pat. No. 2,474,820, when the amino substituent is a heterocycle, including piperazine, the 4-N of the piperazine is unsubstituted, whereas the ring "may or may not be substituted on the carbon atom" (Cf. Col. 10, lines 49-65)

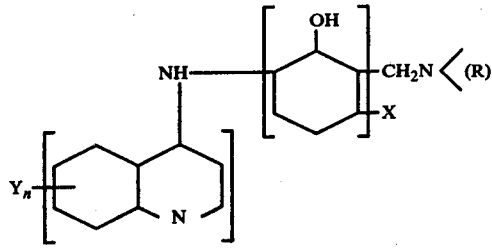

The compounds of the present invention are superior in their use as antihypertensive compounds as they do not display cataractogenic acitivity in the standard laboratory test and thus have a lessened potential of that side effect in man.

The starting compounds of formula I are known. The reactants of formula II are either known or made in the manner shown by Scheme B starting with a nitrobenzyl chloride, which is condensed with a selected 4-substituted piperazino compound V

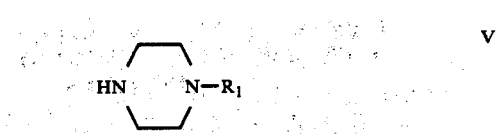

wherein $R_1$ has the significance given above, to give the nitro compound VI, of which the nitro group is reduced to give compound II. Processes for the production of compounds of formula III are further described in the Examples.

Starting compounds of formula IV, wherein R is alkyl of 1 to 3 carbon atoms, can be prepared according to the method of Shiner, et al., *J. Amer. Chem. Soc.*, 90 418(1968).

PREFERRED EMBODIMENT OF THE INVENTION

The alkyl groups in this invention, having 1 to 3 carbon atoms, inclusive, comprise methyl, ethyl and proyl, with methyl preferred.

The preferred halogens are chloro and fluoro.

The pharmacologically acceptable salts of compounds of the formula III comprise the hydrochlorides, hydrobromides, hydriodides, sulfates, phosphates, cyclohexanesulfamates, methanesulfonates, pamoates, and the like, prepared by reacting a compound of formula III with the stoichiometrically calculated amount of the selected pharmacologically acceptable acid.

The compounds III were tested for antihypertensive activity and for cataractogenic activity.

The antihypertensive activity of the new compounds was determined by measuring the mean arterial blood pressure at different dosage levels in the rat and determining from it the mean blood pressure reduction after 4 and 24 hours.

The mean arterial blood pressure is defined in the art as:

$$\frac{\text{systolic pressure} - \text{diastolic pressure}}{3} + \text{diastolic pressure}$$

Also, decrease of the heart rate at 4 and 24 hours after drug administration was determined.

The following is a brief description of the procedures and the basis of reporting compounds as active or inactive hypotensive agents in the assay.

Methods: Chronic abdominal aortic indwelling canula are exteriorized at the nape of the neck of Upjohn Sprague Dawley specific pathogen free female rats. Aortic blood pressure is monitored with a transducer-polygraph system. Mean arterial blood pressure is obtained by electrical integration of the phasic pressure. Heart rate is obtained by electronicaly counting arterial pulses. Two unanesthetized rats are each treated orally with single 50 mg/kg doses of the test compound. These agents are suspended in Upjohn Vehicle 98 [each ml of water contains carboxymethylcellulose (10 mg), polysorbate 80 (4mg) and polyparaben (0.42 mg)] or an appropriate carrier. Injection volume is 10 cc/kg. Mean arterial blood pressure and heart rate are observed before and 4 and 24 hours after drug administration.

Results: Blood pressures of two rats are averaged before, and 4 and 24 hours after oral treatment with the test compound. If the change, initial vs 4 and/or 24 hours, is <5 mm Hg, the compound is considered inactive. Average change is then calculated for two rats. If the decrease is ≧5 mm Hg, the compound is considered to be an active hypotensive agent.

Heart rates are also obtained before, and 4 and 24 hours after drug administration. If the average change, initial vs. 4 and/or 24 hours, is <65 beats per minute, the compound is not considered to have altered the heart rate. If the average change is ≧65 beats per minute, the compound is considered to have altered heart rate.

The compounds of this invention show blood pressure reductions of greater than 10 mm Hg at 4 or 24 hours.

An in vitro test which was used to test for cataractogenic activity of compounds can be found in Edwards, et al, Experimental Eye Research, 10, 228, (1970) and is also described below:

MATERIALS AND METHODS:

Under sterile conditions the commercial *Grand Island Biologicals Co. Medium* #199 containing phenol red at a concentration of 0.002% was diluted 1:10 with sterile distilled water. The diluted Medium #199 was then supplemented with foetal calf serum (10%, v/v), 100 units/ml of penicillin, and 100 mg/ml of streptomycin. The final pH of this growth medium was adjusted with sterile 0.5N sodium hydroxide.

Compounds to be tested were dissolved or suspended at a concentration of 15 mM in Vehicle 124 (0.25% methylcellulose in isotonic saline) containing 10% diluted Medium #199. When necessary, pH adjustments were made to maintain the pH at 7.2.

Eyes were removed from 11-13 day chick embryos in a sterile surface hood. All subsequent steps employed sterile techniques. Lenses were removed and freed of adhering humor. Each lens was then placed into a sterile 12 × 75 mm test tube containing the incubation medium described above. After all lenses were removed, an aliquot (10–100 μl) of Vehicle 124 containing Medium #199 with or without the test compound was added to a final volume of 300 μl. Paired lenses were incubated with different drugs. Each tube was stoppered with gauze-wrapped paper plugs and incubated at 36° C. Lenses were incubated for four hours after which the incubation medium containing the drug was removed by aspiration. Lenses were rinsed once with growth medium and that medium removed; 300 μl of fresh growth medium free of drug was added to the lens and the incubation was continued at 36° C. The pH changes in the growth media were determined semi-quantitatively by color comparison of the tube with a set of standard solutions prepared over the range of pH 4 to 8 and containing the same concentration of phenol red as in the growth medium.

covered. The compounds of this invention (III) did not inhibit respiration, and are thus useful for the treatment for hypertension in mammals, including man.

The pharmaceutical forms of compounds of formula III (Including IIIA and IIIB) and salts thereof contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates, lactose, proteins, lipids, calcium phosphate, cornstarch, stearic acid, methylcellulose and the like may be used as carriers or for coating purposes. Water or oils such as coconut oil, sesame oil, safflower oil, cottonseed oil, and peanut oil, may be used for preparing solutions or suspensions of the active drug. Sweetening, coloring and flavoring agents may be added.

For mammals, food premixes with starch, oatmeal, dried fishmeat, fishmeal, flour, and the like can be prepared.

This invention relates also to pharmaceutical dosage unit forms for systemic administration (oral and parenteral administration) in obtaining unexpectedly advantageous beneficial results in hypertensive conditions in mammals, including humans, and valuable warm-blooded animals such as dogs, cats, and other domestic animals. The term "dosage unit form" as used in this specification and in the claims refers to physically discrete units suitable as unitary dosages for mammalian subjects, each unit containing a predetermined quantity of the essential active ingredient calculated to produce the desired effect in combination with the required pharmaceutical means which adapt the said ingredient for systemic administration. The specification for the novel dosage unit forms of this invention are dictated by and directly dependent on the unique characteristics of the essential active ingredient and the particular effect to be achieved in view of the limitations inherent in the art of compounding such as essential active material for beneficial effects in humans and animals as disclosed in detail in this specification under preferred embodiments, these being features of the present invention.

Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohy-

| Color | Purple | Pink | Slightly Pink | Slightly Orange | Orange | Gold | Light Gold | Yellow |
|---|---|---|---|---|---|---|---|---|
| pH | 8 | 7.2–7.4 | 6.5 | 6 | 5.5 | 5 | 4.5 | 4 |

Color comparisons were made after 17-19 hours, 24 hours and 48 hours. In some experiments comparisons were also made at longer intervals.

As a result of the metabolism by the lenses during incubation, principally due to lactic acid formation, a decrease of the pH and change of color of the indicator from pink to yellow is observed. Thus, by colorometric comparison between pH 4 to 8 of prepared standard solutions any degree of cataractogenic acitivity is disdrates, proteins and mineral solids; for example, starch, sucrose, kaolin, dicalcium phosphate, gelatin, acacia, corn starch, talc, and the like. Capsules both hard and soft are formulated with suitable diluents and excipients; for example, edible oils, talc, calcium carbonate, and the like, and also calcium stearate. Liquid preparations for oral administration are prepared in water or aqueous solutions which advantageously contain suspending agents; for example, sodium carboxymethylcellulose, methylcellulose, acacia, polyvinyl pyrrolidone, polyvinyl alcohol, and the like. In the case of injectable forms, they must be sterile and must be fluid to the extent that easy syringeability exists. Such preparations must be stable under the conditions of manufacture and storage, and ordinarily contain, in addition to the basic solvent or suspending liquid, preservatives in the nature of bactericidal and fungicidal agents; for example, parabens, chlorobutanol, benzyl, alcohol, phenol, and the like. In many cases it is preferable to include isotonic agents; for example, sugars or sodium chloride. Carriers and vehicles include vegetable oils, ethanol, polyols; for example, glycerol, propylene glycol, liquid polyethylene glycol, and the like. Any solid preparations for subsequent extemporaneous preparation of sterile injectable preparations are sterilized, preferably by exposure to a sterilizing gas; for example, ethylene oxide. The aforesaid carriers, vehicles, diluents, excipients, preservatives, isotonic agents, and the like, constitute the pharmaceutical means which adapt the preparations for systemic administration.

The pharmaceutical dosage unit forms are prepared in accordance with the preceding general description to provide from about 5 to about 100 mg of the essential active ingredient per dosage unit form, which, as aforesaid, may be in the form of a solid oral preparation, a liquid oral preparation, an injectable preparation, including liquid preparations and solid dry preparations for extemporaneous reconstitution to a liquid injectable preparation. The amount of the essential active ingredient provided in the pharmaceutical dosage unit forms is that amount sufficient to obtain antihypertensive effects within the effective nontoxic range. Expressed otherwise, an amount of the essential active ingredient is provided to a recipient within a range from about 0.25 mg per kg to about 100 mg per kg of body weight of the recipient, preferably 0.4 to 75 mg per kg; the most preferred dose range is 0.8 to 30 mg per kg.

The amount administered depends on the age, weight, and condition of the patient as determined by the physician.

The following examples are illustrative of the products and processes of the present invention but are not to be construed as limiting.

EXAMPLE 1

4-[[4- [[4- (4-fluorophenyl)piperazinyl ]methyl]-phenyl]amino]-7-(trifluoromethyl)quinoline

A. 1-(4-fluorophenyl)-4-[(4-nitrophenyl)-methyl]piperazine

To a solution of nitrobenzyl chloride (5.2 g, 30 mM) and triethylamine (3.3 g) in 30 ml of ethylene glycol, is added a solution of p-fluorophenylpiperazine (5.4 g, 30 mM) in 20 ml of ethylene glycol at room temperature (20° to 23° C.). After complete addition, the resulting yellow solution is heated to 80° C. under nitrogen. A yellow solid separates after 5 minutes of heating. This is quenched with aqueous 10% sodium carbonate solution and extracted with methylene chloride. The methylene chloride solution is washed with water, then saturated sodium chloride solution, then dried over anhydrous sodium sulfate and concentrated to a yellow solid. This, after recrystallization from ethyl acetate, gives 7.5 g (80%) of yellow crystalline 1-(4-fluorophenyl)-4- [ (4-nitrophenyl)methyl ]piperazine of melting point 139°–141 ° C.

Anal. Calcd. for $C_{17}H_{18}FNO_2$:
Calcd. C, 64.75; H, 5.75; N, 13.32; F, 6.03.
Found C, 64.79; H, 5.77; N, 13.39; F, 5.59.

B. 1-[ (4-aminophenyl)methyl ]-4-(4-fluorophenyl)piperazine

To a suspension of 1-(4-fluorophenyl)-4-[ (4-nitrophenyl)methyl ]piperazine (1.5 g, 0.005 M) in 15 ml of anhydrous ether is added dropwise a solution of 15 ml of titanium trichloride in water (20% solution in water), under nitrogen at room temperature. After complete addition, the mixture is quenched with 10% ammonium hydroxide solution and extracted with methylene chloride. The methylene chloride solution is washed with water, dried (anhydrous sodium sulfate), and concentrated to a yellow solid. This, after recrystallization from ethyl acetate/Skellysolve ® B, gives 900 mg (64%) of white crystalline 1-[ (4-aminophenyl)methyl ]-4-(4-fluorophenyl)piperazine of melting point 130°–132° C.

Anal. Calcd. for $C_{17}H_{20}FN_3$:
Calcd. C, 71.55; H, 7.06; N, 14.73; F, 6.66.
Found C, 71.33; H, 6.93; N, 14.77; F, 6.77.

C. 4-[[4-[[4-(4-fluorophenyl)piperazinyl ]-menthyl ]phenyl ]amino ]-7-(trifluoromethyl)quinoline A solution of 4-chloro-7-trifluoromethylquinoline (762 mg, 0.0035 M), and 2.4 ml of ethanolic hydrogen chloride in 20 ml of ethanol is heated to reflux under nitrogen for 3 hours. The reaction mixture is quenched with cold water, neutralized with 10% aqueous sodium carbonate solution and extracted with methylene chloride. The methylene chloride solution is washed with water, saturated sodium chloride solution, dried (anhydrous sodium sulfate) and concentrated to a white solid. This, after recrystallization from ethyl acetate, gives 1 g (60%) of white crystalline 4-[[4-[[4-(4-fluorophenyl)-piperazinyl ]methyl ]phenyl ]amino ]-7-(trifluoromethyl)quinoline of melting point 216°–217° C.

Anal. Calcd. for $C_{27}H_{24}F_4N_4$:
Calcd. C, 67.49; H, 5.03; N, 11.26; F, 15.82.
Found C, 67.50; H, 5.14; N, 11.58; F, 16.07.

EXAMPLE 2

4-[[4-[[4-(4-methoxyphenyl)-1-piperazinyl ]-methyl ]phenyl ]amino ]-7-(trifluoromethyl) quinoline

A. 1-(4-methoxyphenyl)-4-[(4-nitrophenyl)-methyl]piperazine

A suspension of p-nitrobenzyl chloride (2.58 g, 15 mM), p-methoxyphenylpiperazine dihydrochloride (3.97 g, 15 mM) and triethylamine (4.55 g, 30 mM) in 25 ml of ethylene glycol is heated at 80° C. for 1 hour under nitrogen. The resulting mixture is quenched with cold water, neutralized with 10% aqueous sodium bicarbonate solution and extracted with methylene chloride. The methylene chloride solution is washed with water, saturated sodium chloride solution, dried over sodium sulfate and concentrated to a yellow solid. This, after recrystallization from ethyl acetate, gives 4 g (81%) of 1-(4-methoxyphenyl)-4-[ (4-nitrophenyl)-methyl ]piperazine of melting point 130°–132° C.

B. 1-(4-methoxyphenyl)-4-[ (4-aminophenyl)-methyl ]piperazine

To a suspension of 4-methoxyphenyl-1 -(p-nitrobenzyl)piperazine (3.27 g, 0.01 mol) in 30 ml of ether is added dropwise 30 ml of titanium trichloride (28% aq. solution) at room temperature. After complete addition, the resulting mixture is stirred at room temperature for 1 hour. The mixture is then quenched with ice, made strongly basic with 10% ammonium hydroxide solution and extracted with methylene chloride. The methylene chloride solution is washed with water, dried (over anhydrous sodium sulfate) and concentrated to an oil. The oil is purified by high performance liquid chromatography on silica gel using 5% methanol/95% chloroform as eluant which affords 2 g of white oil; this, after crystallization from ether, gives 1.7 g (57%) of white crystalline 1-(4-methoxyphenyl)-4-[ (4-aminophenyl)methyl ]-piperazine of melting point 100°–102° C.

Anal. Calcd. for $C_{16}H_{23}N_3O$:
Calcd. C, 72.69; H, 7.79; N, 14.13.
Found C, 72.66; H, 7.91; N, 13.98.

C.
4-[[4-[[4-(4-methoxyphenyl)-1-piperazinyl]-methyl]-phenyl]amino]-7-(trifluoromethyl)quinoline A solution of 4-chloro-7-trifluoromethylquinoline (0.976 g, 0.0045 M), 4-methoxyphenyl-1-(p-nitrobenzyl)piperazine (1.34 g, 0.0045 M) and 3 ml of ethanolic hydrogen chloride in 25 ml of ethanol is heated at 80° C. for 4 hours under nitrogen. The reaction mixture is then quenched with cold water, neutralized with aqueous 10% sodium hydroxide solution, extracted with methylene chloride, and concentrated to give a white solid which, after recrystallization from ethyl acetate, affords 1.9 g (86%) of white crystalline 4-[[4-[[4-(methoxyphenyl)-1-piperazinyl]-methyl]phenyl]amino]-7-(trifluoromethyl)quinoline of melting point 235°–237° C.

Anal. Calcd. for $C_{28}H_{27}N_4F_3O$:
Calcd. C, 68.27; H, 5.53; N, 11.38; F, 11.57.
Found C, 68.38; H, 5.72; N, 11.15; F, 11.67.

EXAMPLE 3

4-[[4-[[4-(2-methylphenyl)-1-piperazinyl]methyl]-phenyl]amino]-7-(trifluoromethyl)quinoline

A. 1-(o-tolyl)-4-[4-(p-nitrophenyl)methyl]-piperazine

A suspension of p-nitrobenzyl chloride (2.58 g, 0.015 M), o-tolylpiperazine dihydrochloride (3.73 g, 0.015 M) and triethylamine (4.55 g, 0.03 M) in 25 ml of ethylene glycol is heated at 80° C. for one hour nitrogen. The reaction mixture is then quenched into cold water, neutralized with aqueous 10% sodium carbonate solution and extracted with methylene chloride. The methylene chloride solution is washed with water, saturated sodium chloride solution, dried over anhydrous sodium sulfate and concentrated to a brown oil. This is crystallized from ethyl acetate to give 4 g (86%) of white crystalline 1-(o-tolyl)-4-[4-(p-nitrophenyl)methyl]piperazine of melting point 121°–123° C.

B. 1-(o-tolyl)-4-[(4-aminophenyl)methyl]piperazine

To a suspension of 4-(o-tolyl)-1-(p-nitrobenzyl)piperazine (3.11 g, 0.01 M) in 30 ml of ether is added dropwise 30 ml of titanium trichloride (20% aqueous solution). The resulting mixture is stirred at room temperature for one hour. This is then quenched into cold water, made strongly basic with aqueous 10% ammonium hydroxide solution and extracted with methylene chloride. The methylene chloride solution is washed with water, dried over anhydrous sodium sulfate and concentrated to an oil. This is purified by column chromatography on silica gel to afford 1.3 g (46%) of 1-(o-tolyl)-4-[(4-aminophenyl)methyl]piperazine as an oil.

C. 4-[[4-[[4-(2-methylphenyl)-1-piperazinyl]methyl]-phenyl]amino]-7-(trifluoromethyl)quinoline A solution of 4-chloro-7-trifluoromethyl quinoline (1 g, 0.00216 M), 4-(o-tolyl)-1-p-aminobenzylpiperazine (1.3 g, 0.0046 M) and 3 ml of ethanolic hydrogen chloride in 25 ml of ethanol is heated at reflux for 6 hours under nitrogen. The reaction mixture is quenched with ice water, neutralized with aqueous 10% aqueous sodium hydroxide solution and extracted with methylene chloride. The methylene chloride solution is washed with water, dried over anhydrous sodium sulfate and concentrated to a white solid which, after recyrstallization from ethyl acetate/Skellysolve® B, affords 1.9 g (92%) of white crystalline 4-[[4-[[4-(2-methylpenyl)-1-piperazinyl]methyl]phenyl]amino]-7-(trifluoromethyl)-quinoline of melting point 208°–210° C.

Anal. Calcd. for $C_{28}H_{27}F_3N_4 \cdot \frac{1}{2} H_2O$:
Calcd. C, 69.26; H, 5.81; N, 11.54.
Found C, 69.37; H, 5.84; N, 11.31.

EXAMPLE 4

4-[[4-[[4-(p-methylphenyl)-1-piperazinyl]methyl]-phenyl]amino]-7-(trifluoromethyl)quinoline

A. 1-(p-tolyl)-4-(p-nitrobenzyl)piperazine

In the manner given in Example 1A, p-nitrobenzyl chloride is reacted with p-tolylpiperazine dihydrochloride in the presence of triethylamine to give 1-(p-tolyl)-4-(p-nitrobenzyl)piperazine.

B. 1-(p-tolyl)-4-[(4-aminophenyl)methyl]piperazine

In the manner given in Example 1B, 1-(p-tolyl)-4-(p-nitrobenzyl)piperazine is reduced with aqueous titanium trichloride to give 1-(p-tolyl)-4-[(4-aminophenyl)-methyl]piperazine.

C. 4-[[4-[[4-(p-methylphenyl)-1-piperazinyl]methyl]-phenyl]amino]-7-(trifluoromethyl)quinoline In the manner given in Example 1C, 1-(p-tolyl)-4-[(4-aminophenyl)methyl]piperazine and 4-chloro-7-(trifluoromethyl)quinoline are reacted together at reflux to give 4-[[4-[[4-(p-methylphenyl)-1-piperazinyl]methyl]-phenyl]amino]-7-(trifluoromethyl)quinoline.

EXAMPLE 5

4-[[4-[[4-(p-ethylphenyl)-1-piperazinyl]methyl]phenyl]amino]-7-(trifluoromethyl)quinoline

A. 1-(p-ethylphenyl)-4-(p-nitrobenzyl)piperazine

In the manner given in Example 1A, p-nitrobenzyl chloride is reacted with p-ethylphenylpiperazine dihydrochloride in the presence of triethylamine to give 1-(p-ethylphenyl)-4-(p-nitrobenzyl)piperazine.

B.
1-(p-ethylphenyl)-4-[(4-aminophenyl)methyl]piperazine

In the manner given in Example 1B, 1-(p-ethylphenyl)-4-(p-nitrobenzyl)piperazine is reduced with aqueous titanium trichloride to give 1-(p-ethylphenyl)-4-[(4-aminophenyl)methyl]piperazine.

C.
4-[[4-[[4-(p-ethylphenyl)-1-piperazinyl]methyl]phenyl]amino]-7-(trifluoromethyl)quinoline In the manner given in Example 1C, 1-(p-ethylphenyl)-4-[(4-aminophenyl)methyl]piperazine and 4-chloro-7-(trifluoromethyl)quinoline are reacted together at reflux to give 4-[[4-[[4-(p-ethylphenyl)-1-piperazinyl]methyl]phenyl]amino]-7-(trifluoromethyl)quinoline.

EXAMPLE 6
4-[[4-[[4-(m-methoxyphenyl)-1-piperazinyl]methyl]phenyl]amino]-7-(trifluoromethyl)quinoline

A. 1-(m-methoxyphenyl)-4-(p-nitrobenzyl)piperazine

In the manner given in Example 1A, p-nitrobenzyl chloride is reacted with 4-(m-methoxyphenyl)piperazine dihydrochloride in the presence of triethylamine to give 1-(m-methoxyphenyl)-4-(p-nitrobenzyl)piperazine.

B. 1-(m-methoxyphenyl)-4-[(4-aminophenyl)methyl]piperazine

In the manner given in Example 1B, 1-(m-methoxyphenyl)-4-(p-nitrobenzyl)piperazine is reduced with aqueous titanium trichloride to give 1-(m-methoxyphenyl)-4-[(4-aminophenyl)methyl]piperazine.

C. 4-[[4-[[4-(m-methoxyphenyl)-1-piperazinyl]methyl]phenyl]amino]-7-(trifluoromethyl)quinoline In the manner given in Example 1C, 1-(m-methoxyphenyl)-4-[(4-aminophenyl)methyl]piperazine and 4-chloro-7-(trifluoromethyl)quinoline are reacted together at reflux to give 4-[[4-[[4-(m-methoxyphenyl)-1-piperazinyl]methyl]phenyl]amino]-7-(trifluoromethyl)quinoline.

EXAMPLE 7
4-[[4-[[4-(methyl)-1-piperazinyl]methyl]phenyl]amino]-7-(trifluoromethyl)quinoline

A. 1-methyl-4-[(4-nitrophenyl)methyl]piperazine

To a solution of p-nitrobenzyl chloride (5.2 g, 10mM) and 3.2 g of triethylamine in 30 ml of ethylene glycol is added a solution of N-methylpiperazine (3 g, 30 mM) in 20 ml of ethylene glycol. After complete addition, the resulting solution is heated to 80° C. under nitrogen for 30 minutes. The reaction mixture is quenched into aqueous 10% sodium carbonate solution and extracted with methylene chloride. The methylene chloride solution is washed with water, saturated sodium chloride solution, dried over anhydrous sodium sulfate and concentrated to give 4.15 g (59%) of 1-methyl-4-[(4-nitrophenyl)methyl]piperazine.

B. 1-methyl-4-[(4-aminophenyl)methyl]piperazine

A suspension of 1-[(4-nitrophenyl)methyl]-4-methylpiperazine (3.5 g, 0.015 M) and 700 mg of 5% Pd/C in 200 ml of absolute ethanol is hydrogenated for 20 minutes. This is then filtered, washed with more ethanol and concentrated to a white oil. This is crystallized from acetate/Skellysolve® B to give 900 mg (30%) of white crystalline 1-methyl-4-[(4-aminophenyl)methyl]piperazine.

C. 4-[[4-[(4-methyl-1-piperazinyl)methyl]phenyl]amino]-7-(trifluoromethyl)quinoline A solution of 4-chloro-7-trifluoromethylquinoline (400 mg, 0.0018 M), 1-methyl-4-[(4-aminophenyl)methyl]piperazine (400 mg, 0.0019 M) and 1.4 ml of ethanolic hydrogen chloride in 10 ml of ethanol is heated to reflux, under nitrogen for 15 minutes. The reaction mixture is quenched with ice, neutralized with aqueous 10% sodium hydroxide and extracted with methylene chloride. The methylene chloride solution is washed with water, saturated sodium chloride solution, dried over anhydrous sodium sulfate and concentrated to a white solid. This solid, after recrystallization from ethyl acetate, gives 250 mg (32%) of white crystalline 4-[[4-[(4-methyl-1-piperazinyl)methyl]phenyl]amino]-7-(trifluoromethyl)quioline of melting point 218°–220° C.

Anal. Calcd. for $C_{22}H_{23}F_3N_4$:
Calcd. C, 65.98; H, 5.79; H, 13.99.
Found C, 64.82; H, 5.98; N, 13.44.

EXAMPLE 8
4-[[4-[[4-phenyl-1-piperazinyl]methyl]phenyl]amino]-7-(trifluoromethyl)quinoline

A. 1-phenyl-4-4-[4-(p-nitrobenzyl)]piperazine

In the manner given in Example 1A, p-nitrobenzyl chloride is reacted with 1-phenylpiperazine dihydrochloride in the presence of triethylamine to given 1-phenyl-4-[4-(p-nitrobenzyl)]piperazine.

B. 1-phenyl-4-[(4-aminophenyl)methyl]piperazine

In the manner given in Example 1B, 1-phenyl-4-(p-nitrobenzyl)piperazine is reduced with aqueous titanium trichloride to give 1-phenyl-4-[4-aminophenyl)-methyl]piperazine.

C. 4-[[4-phenyl-1-piperazinyl]methyl]phenyl]amino]-7-(trifluoromethyl)quinoline In the manner given in Example 1C, 1-phenyl-4-[(4-aminophenyl)methyl]piperazine and 4-chloro-7-(trifluoromethyl)quinoline are reacted together at reflux to give 4-[[4-[[4-phenyl-1-piperazinyl]methyl]phenyl]amino]-7-(trifluoromethyl)quinoline.

EXAMPLE 9
4-[[4-[[4-(3-ethylphenyl)-1-piperazinyl]methyl]phenyl]amino]-7-(trifluoromethyl)quinoline

A. 1-(3-ethylphenyl)-4-(p-nitrobenzyl)piperazine

In the manner given in Example 1A, p-nitrobenzyl chloride is reacted with 1-(3-ethylphenyl)piperazine dihydrochloride in the presence of triethylamine to give 1-(3-ethylphenyl)-4-(p-nitrobenzyl)piperazine.

B. 1-(3-ethylphenyl)-4-[(4-aminophenyl)methyl]piperazine

In the manner given in Example 1B, 1-(3-ethylphenyl)-4-(p-nitrobenzyl)piperazine is reduced with aqueous titanium trichloride to give 1-(3-ethylphenyl)-4-[(4-aminophenyl)methyl]piperazine.

C.
4-[[4-[[4-(3-ethylphenyl)-1-piperazinyl]methyl]phenyl]amino]-7-(trifluoromethyl)quinoline In the manner given in Example 1C, 1-(3-ethylphenyl)-4-[(aminophenyl)methyl]piperazine and 4-chloro-7-(trifluoromethyl)quinoline are reacted together at reflux to give 4-[[4-[[4-(3-ethylphenyl)1-piperazinyl]methyl]phenyl]amino]-7-(trifluoromethyl)quinoline.

EXAMPLE 10

4-[[4-[[4-(o-chlorophenyl)-1-piperazinyl]methyl]phenyl]amino]-7-(trifluoromethyl)quinoline A. 1-(o-chlorophenyl)-4-[4-(p-nitrobenzyl)]piperazine In the manner given in Example 1A, p-nitrobenzyl chloride is reacted with 1-(o-chlorophenyl)piperazine dihydrochloride in the presence of triethylamine to give 1-(o-chlorophenyl)-4-[4-(p-nitrobenzyl)]piperazine

B.
1-(o-chlorophenyl)-4-[(4-aminophenyl)methyl]piperazine

In the manner given in Example 1B, 1-(o-chlorophenyl)-4(p-nitrobenzyl)piperazine is reduced with aqueous titanium trichloride to give 1-(o-chlorophenyl)-4-[(4-aminophenyl)]piperazine.

C.
4-[[4-[[4-(o-chlorophenyl)-1-piperazinyl]methyl]phenyl]amino]-7-(trifluoromethyl)quinoline In the manner given in Example 1C, 1-(o-chlorophenyl)-4-[(4-aminophenyl)methyl]piperazine and 4-chloro-7-(trifluoromethyl)quinoline are reacted together at reflux to give 4-[[4-[[4-(o-chlorophenyl)-1-piperazinyl]methyl]phenyl]amino]-7-(trifluoromethyl)quinoline.

EXAMPLE 11

4-[[4-[[4-(m-fluorophenyl)-1-piperazinyl]methyl]phenyl]amino]-7-(trifluoromethyl)quinoline A. 1-fluorophenyl)-4-(p-nitrobenzyl)piperazine In the manner given in Example 1A, p-nitrobenzyl chloride is reacted with 1-(m-fluorophenyl)piperazine dihydrochloride in the presence of triethylamine to give 1-(fluorophenyl)-4-(p-nitrobenzyl)piperazine.

B.
1-(m-fluorophenyl)-4-[(4-aminophenyl)methyl]piperazine

In the manner given in Example 1B, 1-(m-fluorophenyl)-4-(p-nitrobenzyl)piperazine is reduced with aqueous titanium trichloride to give 1-(m-fluorophenyl)-4-[(4-aminophenyl)methyl]piperazine.

C.
4-[[4-[[4-(m-fluorophenyl)-1-piperazinyl]methyl]phenyl]amino]-7-(trifluoromethyl)quinoline In the manner given in Example 1C, 1-(m-fluorophenyl)-[(4-aminophenyl)methyl]piperazine and 4-chloro-7-(trifluoromethyl)quinoline are reacted together at reflux to give 4-[[4-[[4-(m-fluorophenyl)-1-piperazinyl]methyl]phenyl]amino]-7-(trifluoromethyl)quinoline.

EXAMPLE 12

4-[[4-[[4-(4-bromophenyl)-1-piperazinyl]methyl]phenyl]amino]-7-(trifluoromethyl)quinoline A. 1-(4-bromophenyl)-4-(p-nitrobenzyl)piperazine In the manner given in Example 1A, p-nitrobenzyl chloride is reacted with 1-(4-bromophenyl)piperazine dihydrochloride in the presence of triethylamine to give 1-(4-bromophenyl)-4-(p-nitrobenzyl)piperazine

B.
1-(4-bromophenyl)-4-[(4-aminophenyl)methyl]piperazine

In the manner given in Example 1B, 1-(4-bromophenyl)-4-(p-nitrobenzyl)piperazine is reduced with aqueous titanium trichloride to give 1-(4-bromophenyl)-4-[(4-aminophenyl)methyl]piperazine.

C. 4-[[4-[[4-(4-bromophenyl)-4-piperazinyl]methyl]phenyl]amino]-7-(trifluoromethyl)quinoline In the manner given in Example 1C, 1-(4-bromophenyl)-4-[(4-aminophenyl)methyl]piperazine and 4-chloro-7-(trifluoromethyl)quinoline are reacted together at reflux to give 4-[[4-[[4-(4-bromophenyl)-1-piperazinyl]methyl]phenyl]amino]-7-(trifluoromethyl)quinoline.

EXAMPLE 13

4-[[4-[[4-(3,5-dipropoxyphenyl)-1-piperazinyl]methyl]phenyl amino]-7-(trifluoromethyl)quinoline

A.
1-(3,5-dipropoxyphenyl)-4-(p-nitrobenzyl)piperazine.

In the manner given in Example 1A, p-nitrobenzyl chloride is reacted with 1-(3,5-dipropoxyphenyl)piperazine dihydrochloride in the presence of triethylamine to give 1-(3,5-dipropoxyphenyl)4-(p-nitrobenzyl)piperazine.

B.
1-(3,5-dipropoxyphenyl)-4-[(4-aminophenyl)methyl]piperazine

In the manner given in Example 1B, 1-(3,5-dipropoxyphenyl)-4-(p-nitrobenzyl)piperazine is reduced with aqueous titanium trichloride to give 1-(3,5-dipropoxyphenyl)-4-[(4-aminophenyl)methyl]piperazine.

C.
4-[[4-[[4-(3,5-dipropoxyphenyl)-1-piperazinyl]methyl]phenyl]amino]-7-(trifluoromethyl)quinoline In the manner given in Example 1C, 1-(3,5-dipropoxyphenyl)-4-[(4-aminophenyl)methyl]piperazine and 4-chloro-7-(trifluoromethyl)quinoline are reacted together at reflux to give 4-[[4-[[4-(3,5-dipropoxyphenyl)-1-piperazinyl]methyl]phenyl]amino]-7-(trifluoromethyl)quinoline.

EXAMPLE 14

4-[[4-[[4-(3,5-difluorophenyl)-1-piperazinyl]ethyl]phenyl]amino]-7-(trifluoromethyl)quinoline A. 1-(3,5-difluorophenyl)-4-(p-nitrobenzyl)piperazine In the manner given in Example 1A, p-nitrobenzyl chloride is reacted with 4-(3,5-difluorophenyl)piperazine dihydrochloride in the presence of triethylamine to give 1-(3,5-difluorophenyl)-4-(p-nitrobenzyl)piperazine

B.

1-(3,5-difluorophenyl)-4-[(4-aminophenyl)methyl]piperazine

In the manner given in Example 1B, 1-(3,5-difluorophenyl)-4-(p-nitrobenzyl)piperazine is reduced with aqueous titanium trichloride to give 1-(3,5-difluorophenyl)-4-[(4-aminophenyl)methyl-]piperazine.

C.

4-[[4-[[4-(3,5-difluorophenyl)-1-piperazinyl]ethyl]phenyl]amino]-7-(trifluoromethyl)quinoline In the manner given in Example 1C, 1-(3,5-difluorophenyl)-4-[(4-aminophenyl)methyl]piperazine and 4-chloro-7-trifluoromethylquinoline are reacted together at reflux to give 4-[[4-[[4-(3,5-difluorophenyl)-1-piperazinyl]ethyl]phenyl]amino]-7-(trifluoromethyl)quinoline.

EXAMPLE 15

4-[[4-[[4-(2,3-diethylphenyl)-1-piperazinyl]methyl]phenyl]amino]-7-(trifluoromethyl)quinoline A. 1-(2,3-diethylphenyl)-4-(p-nitrobenzyl)piperazine In the manner given in Example 1A, p-nitrobenzyl chloride is reacted with (2,3-diethylphenyl)piperazine dihydrochloride in the presence of triethylamine to give 1-(2,3-diethylphenyl)-4-(p-nitrobenzyl)piperazine.

B.

1-(2,3-diethylphenyl)-4-[(4-aminophenyl)methyl]piperazine

In the manner given in Example 1B, 1-(2,3-diethylphenyl)-4-(p-nitrobenzyl)piperazine is reduced with aqueous titanium trichloride to give 1-(2,3-diethylphenyl)-4-[(4-aminophenyl)methyl]piperazine.

C.

4-[[4-[[4-(2,3-diethylphenyl)-1-piperazinyl]methyl]phenyl]amino]-7-(trifluoromethyl)quinoline In the manner given in Example 1C, 1-(2,3-diethylphenyl)-4-[(4-aminophenyl)methyl]piperazine and 4-chloro-7-(trifluoromethyl)quinoline are reacted together at reflux to give 4-[[4-[[4-(2,3-diethylphenyl)-1-piperazinyl]methyl]phenyl]amino]-7-(trifluoromethyl)quinoline.

EXAMPLE 16

4-[[4-[[4-(m-methoxyphenyl)-1-piperazinyl]methyl]phenyl]amino]-7-chloroquinoline A. 1-(m-methoxyphenyl)-4-(p-nitrobenzyl)piperazine In the manner given in Example 1A, p-nitrobenzyl chloride is reacted with (m-methoxyphenyl)piperazine dihydrochloride in the presence of triethylamine to give 1-(m-methoxyphenyl)-4-(p-nitrobenzyl)piperazine.

B.

1-(m-methoxyphenyl)-4-[(4-aminophenyl)methyl]piperazine

In the manner given in Example 1B, 4-[4-(p-nitrobenzyl)]piperazine is reduced with aqueous titanium trichloride to give 1-(m-methoxyphenyl)4-[(4-aminophenyl)methyl]piperazine.

C.

4-[[4-[[4-(m-methoxyphenyl)-1-piperazinyl]methyl]phenyl]amino]-7-chloroquinoline In the manner given in Example 1C, 1-(m-methoxyphenyl)-4-[(4-aminophenyl)methyl]piperazine and 4,7-dichloroquinoline are reacted together at reflux to give 4-[[4-[[4-(m-methoxyphenyl)-1-piperazinyl]methyl]phenyl]amino]-7-chloroquinoline.

EXAMPLE 17

4-[[4-[[4-phenyl-1-piperazinyl]methyl]phenyl]amino]-7-(chloro)quinoline

A. 1-phenyl-4-(p-nitrobenzyl)piperazine

In the manner given in Example 1A, p-nitrobenzyl chloride is reacted with phenylpiperazine dihydrochloride in the presence of triethylamine to give 1-phenyl-4-(p-nitrobenzyl)piperazine B. 1-phenyl-4-[(4-aminophenyl)methyl]piperazine In the manner given in Example 1B, 1-phenyl-4-(p-nitrobenzyl)piperazine is reduced with aqueous titanium trichloride to give 1-phenyl-4-[(4-aminophenyl)methyl]piperazine.

C.

4-[[4-[[4-phenyl-1-piperazinyl]methyl]phenyl]amino]-7-(chloro)quinoline

In the manner given in Example 1C, 1-phenyl-4-[(4-aminophenyl)methyl]piperazine and 4,7-dichloroquinoline are reacted together at reflux to give 4-[[4-[[4-phenyl-1-piperazinyl]methyl]phenyl]amino]-7-(chloro)quinoline.

EXAMPLE 18

4-[[4-[[4-(3,5-dibromophenyl)-1-piperazinyl]methyl]phenyl]amino]-7-(trifluoromethyl)quinoline A. 1-(3,5-dibromophenyl)-4-(p-nitrobenzyl)piperazine In the manner given in Example 1A, p-nitrobenzyl chloride is reacted with (3,5-dibromophenyl)piperazine dihydrochloride in the presence of triethylamine to give 1-(3,5-dibromophenyl)-4-(p-nitrobenzyl)piperazine.

B.

1-(3,5-dibromophenyl)-4-[(4-aminophenyl)methyl]piperazine

In the manner given in Example 1B, 1-(3,5-dibromophenyl)-4-(p-nitrobenzyl)piperazine is reduced with aqueous titanium trichloride to give 1-(3,5-dibromophenyl)-4-[(4-aminophenyl)methyl]piperazine.

C.

4-[[4-[[4-(3,5-dibromophenyl)-1-piperazinyl]methyl]phenyl]amino]-7-(trifluoromethyl)quinoline In the manner given in Example 1C, 1-(3,5-dibromophenyl)-4-[(4-aminophenyl)methyl]piperazine and 4-chloro-7-(trifluoromethyl)quinoline are reacted together at reflux to give 4-[[4-[[4-(3,5-dibromophenyl)-1-piperazinyl]methyl]phenyl]amino]-7-(trifluoromethyl)quinoline.

EXAMPLE 19

4-[[4-[[4-(2,5-dichlorophenyl)-1-piperazinyl]methyl]-phenyl]amino]-7-(trifluoromethyl)quinoline A. 1-(2,5-dichlorophenyl)-4-(p-nitrobenzyl) piperazine In the manner given in Example 1A, p-nitrobenzyl chloride is reacted with (2,5-dichlorophenyl)piperazine dihydrochloride in the presence of triethylamine to give 1-(2,5-dichlorophenyl)-4-(p-nitrobenzyl)piperazine.

B.

1-(2,5-dichlorophenyl)-4-[(4-aminophenyl)methyl]piperazine

In the manner given in Example 1B, 1-(2,5-dichlorophenyl)-4-(p-nitrobenzyl)piperazine is reduced with aqueous titanium trichloride to give 1-(2,5-dichlorophenyl)-4-[(4-aminophenyl)methyl]piperazine.

C.

4-[[4-[[4-(2,5-dichlorophenyl)-1-piperazinyl]methyl]-phenyl]amino]-7-(trifluoromethyl)quinoline In the manner given in Example 1C, 1-(2,5-dichlorophenyl)-4-[(4-aminophenyl)methyl]piperazine and 4-chloro-7-(trifluoromethyl)quinoline are reacted together at reflux to give 4-[[4-[[4-(2,5-dichlorophenyl)-1-piperazinyl]methyl]phenyl]amino]-7-(trifluoromethyl)-quinoline.

EXAMPLE 20

4-[[4-[[4-(p-fluorophenyl)-1-piperazinyl]methyl]phenyl]amino]-7-chloroquinoline

A. 1-(p-fluorophenyl)-4-(p-nitrobenzyl)piperazine

In the manner given in Example 1A, p-nitrobenzyl chloride is reacted with 1-(p-fluorophenyl)piperazine dihydrochloride in the presence of triethylamine to give 1-(p-fluorophenyl)-4-(p-nitrobenzyl)piperazine

B.

1-(p-fluorophenyl)-4-[(4-aminophenyl)methyl]piperazine

In the manner given in Example 1B, 1-(p-fluorophenyl)-4-(p-nitrobenzyl)piperazine is reduced with aqueous titanium trichloride to give 1-(p-fluorophenyl)-4-[(4-aminophenyl)methyl]piperazine.

C.

4-[[4-[[4-(p-fluorophenyl)-1-piperazinyl]methyl]phenyl]amino]-7-chloroquinoline

In the manner given in Example 1C, 1-(p-fluorophenyl)-4-[(4-aminophenyl)methyl]piperazine and 4,7-dichloroquinoline are reacted together at reflux to give 4-[[4-[[4-(p-fluorophenyl)-1-piperazinyl]methyl]phenyl]amino]-7-chloroquinoline.

EXAMPLE 21

4-[[4-[1-[4-(p-methylphenyl)-1-piperazinyl]ethyl]-phenyl]amino]-7-(trifluoromethyl)quinoline

A.

1-(p-methylphenyl)-4-[1-(p-nitrophenyl)ethyl]piperazine

In the manner given in Example 1A, 1-(p-nitrophenyl)-1-chloroethane is reacted with (p-methylphenyl)piperazine dihydrochloride in the presence of triethylamine to give 1-(4-methylphenyl)-4-[1-(p-nitrophenyl)ethyl]piperazine.

B.

1-(4-methylphenyl)-4-[1-(p-aminophenyl)ethyl]piperazine

In the manner given in Example 1B, 1-(4-methylphenyl)-4-[1-(4-nitrophenyl)ethyl]piperazine is reduced with aqueous titanium trichloride to give 1-(4-methylphenyl)-4-[1-(p-aminophenyl)ethyl]piperazine.

C.

4-[[4-[1-[4-(p-methylphenyl)-1-piperazinyl]ethyl]-phenyl]amino]-7-(trifluoromethyl)quinoline In the manner given in Example 1C, 1-(4-methylphenyl)-4-[1-(4-aminophenyl)ethyl]piperazine and 4-chloro-7-(trifluoromethyl)quinoline are reacted together at reflux to give 4-[[4-[1-[4-(p-methylphenyl)-1-piperazinyl]ethyl]phenyl]amino]-7-(trifluoromethyl)-quinoline.

EXAMPLE 22

4-[[4-[1-[4-(p-fluorophenyl)-1-piperazinyl]propyl]-phenyl]amino]-7-(trifluoromethyl)quinoline

A.

1-(p-fluorophenyl)-4-[1-(p-nitrobenzyl)propyl]piperazine

In the manner given in Example 1A, 1-(p-nitrophenyl)-1-chloropropane is reacted with (p-fluorophenyl)piperazine dihydrochloride in the presence of triethylamine to give 1-(p-fluorophenyl)-4-[1-(4-nitrophenyl)propyl]piperazine.

B.

1-(p-fluorophenyl)-4-[1-(4-aminophenyl)propyl]piperazine

In the manner given in Example 1B, 1-(p-fluorophenyl)-4-[1-(4-nitrophenyl)propyl]piperazine is reduced with aqueous titanium trichloride to give 1-(4-fluorophenyl)-4-[1-(4-aminophenyl)propyl]piperazine.

C.

4-[[4-[1-[4-(p-fluorophenyl)-1-piperazinyl]propyl]-phenyl]amino]-7-(trifluoromethyl)quinoline In the manner given in Example 1C, 1-(p-fluorophenyl)-4-[1-(4-aminophenyl)propyl]piperazine and 4-chloro-7-(trifluoromethyl)quinoline are reacted together at reflux to give 4-[[4-[1-[4-(p-fluorophenyl)-1-piperazinyl]propyl]phenyl]amino]-7-(trifluoromethyl)-quinoline.

EXAMPLE 23

4-[[4-[1-[4-(p-methylphenyl)-1-piperazinyl]ethyl]-phenyl]amino]-7-chloroquinoline

A.

1-(p-methylphenyl)-4-[1-(p-nitrophenyl)ethyl]piperazine

In the manner given in Example 1A, 1-(p-nitrophenyl)-1-chloroethane is reacted with (p-methylphenyl)piperazine dihydrochloride in the presence of triethylamine to give 1-(p-methylphenyl)-4-[1-(p-nitrophenyl)ethyl]piperazine.

B.

1-(p-methylphenyl)-4-[1-(p-aminophenyl)methyl]piperazine

In the manner given in Example 1B, 1-(p-methylphenyl)-4-[1-(p-nitrophenyl)ethyl]piperazine is reduced with aqueous titanium trichloride to give 1-(p-methylphenyl)-4-[1-(p-aminophenyl)ethyl]piperazine.

C.

4-[[4-[1-[4-(methylphenyl)-1-piperazinyl]ethyl]phenyl]amino]-7-chloroquinoline

In the manner given in Example 1C, 1-(p-methylphenyl)-4-[1-(p-aminophenyl)ethyl]piperazine and 4,7-dichloroquinoline are reacted together at reflux to give 4-[[4-[1-[4-(p-methylphenyl)-1-piperazinyl]ethyl]phenyl]amino]-7-chloroquinoline.

In the manner given in Examples 1A through 1C, other compounds of formula III can be prepared. Representative compounds thus prepared include:

4-[[4-[[4-(2,4-dimethylphenyl)-1-piperazinyl]methyl]phenyl]amino]-7-(trifluoromethyl)quinoline;
4-[[4-[[4-(2,4-dipropylphenyl)-1-piperazinyl]methyl]phenyl]amino]-7-(trifluoromethyl)quinoline;
4-[[4-[[4-(4-trifluoromethylphenyl)-1-piperazinyl]methyl]phenyl]amino]-7-(trifluoromethyl)quinoline;
4-[[4-[[4-(2,3-dichlorophenyl)-1-piperazinyl]methyl phenyl]amino]-7-(trifluoromethyl)quinoline;
4-[[4-[[4-(2,4-dibromophenyl)-1-piperazinyl]methyl]phenyl]amino]-7-(trifluoromethyl)quinoline;
4-[[4-[[4-(2,5-diethoxyphenyl)-1-piperazinyl]methyl]phenyl]amino]-7-(trifluoromethyl)quinoline;
4-[[4-[[4-(2,4-dimethylphenyl)-1-piperazinyl]methyl]phenyl]amino]-7-(chloro)quinoline;
4-[[4-[[4-(4-trifluoromethylphenyl)-1-piperazinyl]methyl]phenyl]amino]-7-(chloro)quinoline;
4-[[4-[[4-(2,4-difluorophenyl)-1-piperazinyl]methyl]phenyl]amino]-7-(chloro)quinoline;
4-[[4-[[4-(2,3-dichlorophenyl)-1-piperazinyl]methyl]phenyl]amino]-7-(chloro)quinoline;
4-[[4-[[4-(2,4-dibromophenyl)-1-piperazinyl]methyl]phenyl]amino]-7-(chloro)quinoline;
4-[[4-[[4-(3-bromophenyl)-2-piperazinyl]-methyl]phenyl]amino]-7-(chloro)quinoline;
4-[[4-[[4-(2,5-diethoxyphenyl)-1-piperazinyl]methyl]phenyl]amino]-7-(chloro)quinoline;
4-[[4-[1-[4-(m-ethylphenyl)-1-piperazinyl]ethyl]phenyl]amino]-7-(trifluoromethyl)quinoline;
4-[[4-[1-[4-(3,5-diethylphenyl)-1-piperazinyl]ethyl]phenyl]amino]-7-(trifluoromethyl)quinoline;
4-[[4-[1-[4-(2,4-dichlorophenyl)-1-piperazinyl]ethyl]phenyl]amino]-7-(trifluoromethyl)quinoline;
4-[[4-[1-[4-(2,5-dibromophenyl)-1-piperazinyl]ethyl]phenyl]amino]-7-(trifluoromethyl)quinoline;
4-[[4-[1-[4-(o-propoxyphenyl)-1-piperazinyl]ethyl]phenyl]amino]-7-(trifluoromethyl)quinoline;
4-[[4-[1-[4-(m-ethoxyphenyl)-1-piperazinyl]ethyl]phenyl]amino]-7-(trifluoromethyl)quinoline;
4-[[4-[1-[4-(p-propylphenyl)-1-piperazinyl]ethyl]phenyl]amino]-7-(trifluoromethyl)quinoline;
4-[[4-[1-[4-(p-fluorophenyl)-1-piperazinyl]ethyl]phenyl]amino]-7-(trifluoromethyl)quinoline;
4-[[4-[1-[4-(phenyl)-1-piperazinyl]ethyl]phenyl]amino]-7-(trifluoromethyl)quinoline;
4-[[4-[1-[4-(m-ethylphenyl)-1-piperazinyl]ethyl]phenyl]amino]-7-chloroquinoline;
4-[[4-[1-[4-(3,5-diethylphenyl)-1-piperazinyl]ethyl]phenyl]amino]-7-chloroquinoline;
4-[[4-[1-[4-(3-chlorophenyl)-1-piperazinyl]ethyl]phenyl]amino]-7-chloroquinoline;
4-[[4-[1-[4-(2,5-dibromophenyl)-1-piperazinyl]ethyl]phenyl]amino]-7-chloroquinoline;
4-[[4-[1-[4-(o-propoxyphenyl)-1-piperazinyl]ethyl]phenyl]amino]-7-chloroquinoline;
4-[[4-[1-[4-(m-ethoxyphenyl)-1-piperazinyl]ethyl]phenyl]amino]-7-chloroquinoline;
4-[[4-[1-[4-(p-propylphenyl)-1-piperazinyl]ethyl]phenyl]amino]-7-chloroquinoline;
4-[[4-[1-[4-(p-fluorophenyl)-1-piperazinyl]ethyl]phenyl]amino]-7-chloroquinoline;
4-[[4-[1-[4-(phenyl)-1-piperazinyl]ethyl]phenyl]amino]-7-chloroquinoline;

and the like.

Treating the compounds of formula III with pharmacologically acceptable acids such as hydrochloric, hydrobromic, phosphoric, sulfuric, acetic, propionic, toluenesulfonic, methanesulfonic, tartaric, citric, lactic, malic, maleic, pamoic and cyclohexanesulfamic acids produces the pharmacologically acceptable salts of these compounds of formula III which can be used like the free base compounds of formula II. Salt formation is achieved in conventional manner by reacting the compounds of formula III with excess of a selected acid in a suitable medium, e.g., water, a lower alkanol, ether, or acetone and recovering the salt by evaporating the solvent, preferably in vacuo.

The following examples set forth illustrative formulations which are useful for the practice of this invention:

EXAMPLE 24

One thousand tablets for oral use, each containing 50 mg of 4-[[4-[[4-(p-fluorophenyl)-1-piperazinyl]methyl]phenyl]amino]-7-trifluoromethylquinoline as essential active ingredients are prepared from the following ingredients:

| Essential active ingredient | 50 g |
|---|---|
| Dicalcium phosphate | 150 g |
| Methylcellulose, U.S.P. (15 cps) | 6.5 g |
| Talc | 20 g |
| Calcium stearate | 2.5 g |

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of severe hypertension in adult humans at a dose of 1 tablet 3 or 4 times a day.

EXAMPLE 25

One thousand two-piece hard gelatin capsules for oral use, each capsule containing 75 mg of 4-[[4-[[4-(p-methoxyphenyl)-1-piperazinyl]methyl]phenyl]amino]-7-trifluoromethylquinoline as essential active ingredient are prepared from the following ingredients:

| Essential active ingredient | 75 g |
|---|---|
| Lactose, U.S.P. | 100 g |
| Starch, U.S.P. | 10 g |
| Talc, U.S.P. | 5 g |
| Calcium stearate | 1 g |

The finely powdered materials are mixed thoroughly, then filled into hard gelatin capsules of appropriate size.

A satisfactory clinical response is obtained in adults showing hypertension with 1 capsule 4 times a day.

EXAMPLE 26

An aqueous oral preparation containing in each teaspoonful (5 ml) 30 mg of 4-[[4-[[4-(p-fluorophenyl)-1-piperazinyl]methyl]phenyl]amino]-7-trifluoromethylquinoline as essential active ingredient is prepared from the following ingredients:

| | |
|---|---|
| Essential active ingredient hydrochloride | 70 g |
| Methylparaben, U.S.P. | 7.5 g |
| Propylparaben, U.S.P. | 2.5 g |
| Saccarin sodium | 12.5 g |
| Cyclamate sodium | 2.5 g |
| Glycerin | 3000 g |
| Tragacanth powder | 10 g |
| Orange oil flavor | 10 g |
| F.D. and C. Orange dye | 7.5 g |
| Deionized water, q.s. to | 10,000 ml |

The foregoing aqueous preparation is useful in the treatment of adult hypertension at a dose of 1 teaspoonful 4 times a day.

EXAMPLE 27

One thousand tablets for oral administration, each containing 10 mg of 4-[[4-[[4-(p-fluorophenyl)-1-piperazinyl]methyl]phenyl]amino]-7-trifluoromethylquinoline as active ingredient and 16.2 mg of phenobarbital are prepared from the following ingredients:

| | |
|---|---|
| Essential active ingredient, micronized | 10 g |
| Phenobarbital | 16.2 g |
| Lactose | 150 g |
| Starch | 15 g |
| Magnesium stearate | 1.5 g |

The ingredients are thoroughly mixed and slugged. The slugs are broken down by forcing through a screen and the resulting granules are then compressed into tablets.

These tablets are useful in lowering the blood pressure of dogs at a dose of 2 to 3 tablets depending on the weight of the animal and its condition.

EXAMPLE 28

One thousand suppositories, each weighing 2.5 g and containing 100 mg of 4-[[4-[[4-(p-methoxyphenyl)-1-piperazinyl]methyl]phenyl]amino]-7-trifluoromethylquinoline as essential active ingredient are prepared from the following ingredients:

| | |
|---|---|
| Essential active ingredient | 100 g |
| Propylene glycol | 165 g |
| Polyethylene glycol 4000 q.s. | 2500 g |

The essential active ingredient is added to the propylene glycol and the mixture milled until uniformly dispersed. The PEG 4000 is melted and the propylene glycol dispersion added. The suspension is poured into molds and allowed to cool and solidify.

These suppositories are useful in the treatment of hypertension at a dose of 1 suppository rectally three times a day.

EXAMPLE 29

One thousand hard gelatin capsules for oral use, each containing 50 mg of 4-[[4-[[4-(p-fluorophenyl)-1-piperazinyl]methyl]phenyl]amino]-7-trifluoromethylquinoline as essential active ingredient and 25 mg of hydrochlorothiazide are prepared from the following ingredients:

| | |
|---|---|
| Essential active ingredient, micronized | 50 g |
| Hydrochlorothiazide | 25 g |
| Starch | 125 g |
| Talc | 25 g |

One capsule 4 times a day is useful in the relief of moderate hypertension in adult humans.

EXAMPLE 30

Ten thousand tablets for oral use, each containing 40 mg of 4-[[4-[[4-(4-methoxyphenyl)-1-piperazinyl]methyl]phenyl]amino]-7-trifluoromethylquinoline as essential active ingredient and 320 mg acetaminophen are prepared from the following ingredients and using the procedure of Example 27

| | |
|---|---|
| Essential active ingredient finely powdered | 400 g |
| Acetaminophen, finely powdered | 3200 g |
| Corn starch | 500 g |
| Talc | 500 g |
| Calcium stearate | 50 g |

This tablet is useful in treating hypertension in an adult patient by administering one or two tablets 3 times a day depending on the severity of the condition.

Although not necessary in the embodiments of the inventive concept, additional active ingredients are incorporated in the present pharmaceutical dosage unit forms as desired. Each pharmaceutical dosage unit form contains therein an amount within the following nontoxic effective ranges: antihypertensive and diuretic agents such as reserpine (0.05 to 1 mg), hydralazine (10 to 100 mg), methyldopa (100 to 250 mg), guanethidine (10 to 50 mg), hydrochlorothiazide (15 to 50 mg) and ethoxzolamide (50 to 150 mg); tranquilizers, antipsychotic and anti-anxiety agents such as chlorpromazine (5 to 50 mg), thioridazine (5 to 100 mg), haloperidol (0.5 to 5 mg), meprobamate (100 to 400 mg), chlordiazepoxide (5 to 50 mg), diazepam (2 to 15 mg) and ectylurea (100 to 300 mg); barbiturates such as phenobarbital (8 to 60 mg), butabarbital (8 to 60 mg) and amobarbital (16 to 120 mg); analgesics such as aspirin (150 to 600 mg) and acetaminophen (150 to 600 mg); or antidepressants such as amitriptyline hydrochloride (10 to 50 mg), methylphenidate hydrochloride (5 to 20 mg), d-amphetamine sulfate (2 to 15 mg), methamphetamine hydrochloride (2 to 15 mg) and melitracen (15 to 50 mg).

I claim:
1. A compound of the formula III

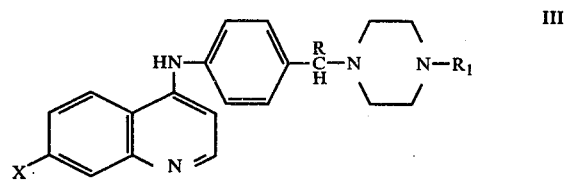

wherein X is chloro or trifluoromethyl; wherein R is hydrogen or alkyl of 1 to 3 carbon atoms, inclusive; wherein R$_1$ is phenyl, or phenyl substituted with one or two alkyl, alkoxy, trifluoromethyl or halo substituents in which alkyl and alkoxy are each of 1 to 3 carbon atoms, inclusive; and halo is fluoro, chloro or bromo, or the pharmacologically acceptable acid addition salts thereof.

2. The compound according to claim 1 of the formula IIIA

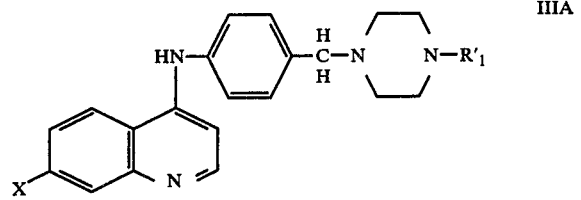

wherein X is chloro or trifluoromethyl; wherein R'₁ is phenyl or phenyl substituted with one or two alkyl, alkoxy, trifluoromethyl, halo substituents in which alkoxy and alkyl are each of 1 to 3 carbon atoms, inclusive, and halo is fluoro, chloro or bromo, or the pharmacologically acceptable acid addition salts thereof.

3. The compound according to claim 1 of the formula IIIB

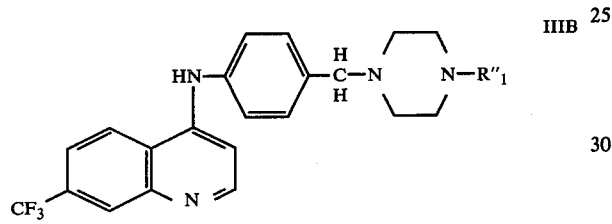

wherein R″₁ is phenyl substituted by one or two alkyl, alkoxy or halo substituents in which alkyl and alkoxy are each of 1 to 3 carbon atoms, inclusive, and halo is fluoro or chloro, or the pharmacologically acceptable acid addition salts thereof.

4. The compound according to claim 3 wherein R″₁ is p-methoxyphenyl and the compound is therefore 4-[[4-[[4-(p-methoxyphenyl)-1-piperazinyl]methyl]phenyl]amino]-7-(trifluoromethyl)quinoline.

5. The compound according to claim 3 wherein R″₁ is p-trifluoromethylphenyl and the compound is therefore 4-[[4-[[4-(p-(trifluoromethyl)phenyl]-1-piperazinyl]methyl]phenyl]amino]-7-(trifluoromethyl)quinoline.

6. The compound according to claim 3 wherein R″₁ is 2-methylphenyl and the compound is therefore 4-[[4-[[4-(2-methylphenyl)-1-piperazinyl]methyl]phenyl]amino]-7-(trifluoromethyl)quinoline.

7. A compound according to claim 3 wherein R″₁ is p-methylphenyl and the compound is therefore 4-[[4-[[4-(p-methylphenyl)-1-piperazinyl]methyl]phenyl]amino]-7-(trifluoromethyl)quinoline.

8. A compound according to claim 3 wherein R″₁ is p-ethylphenyl and the compound is therefore 4-[[4-[[4-(p-ethylphenyl)-1-piperazinyl]methyl]phenyl]amino]-7-(trifluoromethyl)quinoline.

9. A compound according to claim 2 wherein R'₁ is phenyl and the compound is therefore 4-[[4-[[4-(phenyl)-1-piperazinyl]methyl]phenyl]amino]-7-(trifluoromethyl)quinoline.

10. A compound according to claim 3 wherein R″₁ is o-chlorophenyl and the compound is therefore 4-[[4-[[4-(o-chlorophenyl)-1-piperazinyl]methyl]phenyl]amino]-7-(trifluoromethyl)quinoline.

11. A compound according to claim 3 wherein R″₁ is p-fluorophenyl and the compound is therefore 4-[[4-[[4-(p-fluorophenyl)-1-piperazinyl]methyl]phenyl]amino]-7-(trifluoromethyl)quinoline.

12. A compound according to claim 3 wherein R″₁ is 3,5-dipropoxyphenyl and the compound is therefore 4-[[4-[[4-(3,5-dipropoxyphenyl)-1-piperazinyl]methyl]phenyl]amino]-7-(trifluoromethyl)quinoline.

13. A compound according to claim 3 wherein R″₁ is 3,5-difluorophenyl and the compound is therefore 4-[[4-[[4-(3,5-difluorophenyl)-1-piperazinyl]methyl]phenyl]amino]-7-(trifluoromethyl)quinoline.

14. A compound according to claim 2 wherein R'₁ is 3,5-dibromophenyl and the compound is therefore 4-[[4-[[4-(3,5-dibromophenyl)-1-piperazinyl]methyl]phenyl]amino]-7-(trifluoromethyl)quinoline.

15. A pharmaceutical dosage unit form for systemic administration to alleviate hypertension consisting essentially of an effective nontoxic amount of a compound of the formula III

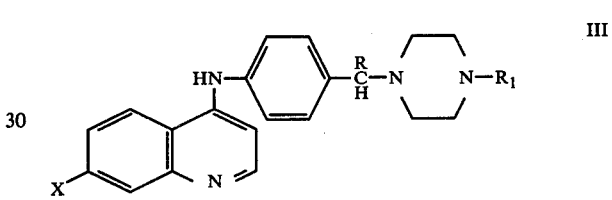

wherein X is chloro or trifluoromethyl; wherein R is hydrogen or alkyl of 1 to 3 carbon atoms, inclusive; wherein R₁ is phenyl, or phenyl substituted with one or two alkyl, alkoxy, trifluoromethyl or halo substituents in which alkyl and alkoxy are each of 1 to 3 carbon atoms, inclusive; and halo is fluoro, chloro or bromo, or the pharmacologically acceptable acid salts thereof, in association with a pharmaceutical carrier.

16. A pharmaceutical composition according to claim 15 wherein the compound used in effective nontoxic amount is that of formula IIIA

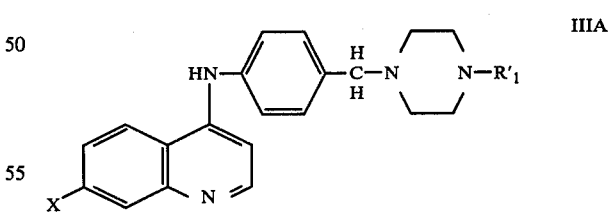

wherein X is chloro or trifluoromethyl; wherein R'₁ is phenyl or phenyl substituted with one or two alkyl, alkoxy, trifluoromethyl, or halo substituents in which alkyl and alkoxy are each of 1 to 3 carbon atoms, inclusive, and halo is fluoro, chloro or bromo, or the pharmacologically acceptable acid addition salts thereof.

17. A pharmaceutical composition according to claim 15 wherein the compound used in effective nontoxic amount is that of the formula IIIB

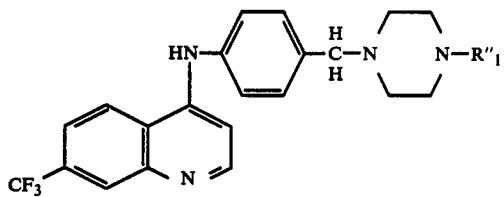

wherein R''₁ is substituted by one or two alkyl, alkoxy or halo substituents in which alkyl and alkoxy are each of 1 to 3 carbon atoms, inclusive, and halo is fluoro or chloro, or the pharmacologically acceptable acid addition salts thereof.

18. A pharmaceutical composition according to claim 17 wherein the compound used in effective nontoxic amount is 4-[[4-[[4-(p-fluorophenyl)-1-piperazinyl]methyl]phenyl]amino]-7-(trifluoromethyl)quinoline, or its pharmaceutically acceptable acid addition salt.

19. A method of obtaining antihypertensive effects in a mammal which consists essentially of administering systemically to the mammal a pharmaceutical dosage unit form supplying an effective nontoxic amount for antihypertensive effects of a compound of the formula III

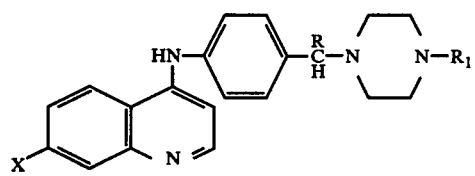

wherein X is chloro or trifluoromethyl; wherein R is hydrogen or alkyl of 1 to 3 carbon atoms, inclusive; wherein R₁ is phenyl, or phenyl substituted with one or two alkyl, alkoxy, trifluoromethyl or halo substituents in which alkyl and alkoxy are each of 1 to 3 carbon atoms, inclusive; and halo is fluoro, chloro or bromo, or the pharmacologically acceptable acid salts thereof.

20. A method according to claim 19 wherein the compound is of the formula IIIA

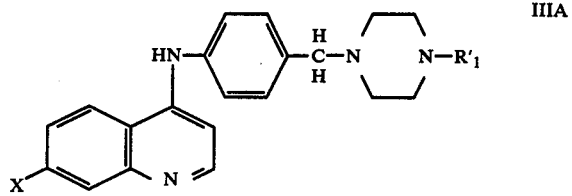

wherein X is chloro or trifluoromethyl; wherein R'₁ is phenyl or phenyl substituted with one or two alkyl, alkoxy, trifluoromethyl, or halo substituents in which alkyl and alkoxy are each of 1 to 3 carbon atoms, inclusive, and halo is fluoro, chloro or bromo, or the pharmacologically acceptable acid addition salts thereof.

21. A method according to claim 19 wherein the compound is of the formula IIIB

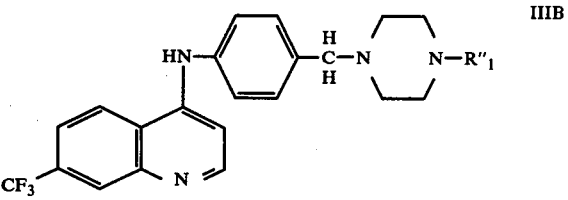

wherein R''₁ is phenyl substituted by one or two alkyl, alkoxy or halo substituents in which alkyl and alkoxy are each of 1 to 3 carbon atoms, inclusive, and halo is fluoro or chloro, or the pharmacologically acceptable acid addition salts thereof.

22. A method according to claim 21 wherein the compound is 4-[[4-[[4-(p-fluorophenyl)-1-piperazinyl]methyl]phenyl]amino]-7-(trifluoromethyl)quinoline, or its pharmacologically acceptable acid addition salt.

* * * * *

UNITED STATES PATENT OFFICE
CERTIFICATE OF CORRECTION

Patent No. 4,140,775          Dated 20 Febraury 1979

Inventor(s) John M. McCall

It is certified that error appears in the above-identified patent and that said Letters Patent are hereby corrected as shown below:

Column 5, line 1, "$\geq$5" should read -- $>$5 --; line 7, "$\geq$65" should read -- $>$65 --;
Column 8, line 25, "menthyl" should read -- methyl --;
Column 9, line 47, "one hour nitrogen" should read -- one hour under nitrogen --;

Column 12, line 29, "1-phenyl-4-4-[4-(p-nitrobenzyl]piperazine" should read -- 1-phenyl-4-[4-(p-nitrobenzyl)]piperazine --; line 39, "1-phenyl-4-[4-" should read -- 1-phenyl-4-[(4- --; line 43, "4-[[4-phenyl-" should read 4-[[4-[[4-phenyl- --; line 56 and 60, "-4-(p-nitrobenzyl)" should read -- -4-[4-(p-nitrobenzyl) --;
Column 13, line 29, [(4-aminophenyl)]piperazine" should read -- [(4-aminophenyl)]methyl]piperazine --; line 45, "1-fluorophenyl)-" should read -- 1-(fluorophenyl)- --;
Column 14, line 32, "phenyl amino]-" should read -- phenyl]amino] --.

Signed and Sealed this

Twenty-second Day of January 1980

[SEAL]

Attest:

SIDNEY A. DIAMOND

Attesting Officer      Commissioner of Patents and Trademarks